US009370474B2

(12) United States Patent
Johnson et al.

(10) Patent No.: US 9,370,474 B2
(45) Date of Patent: *Jun. 21, 2016

(54) HIGH-CLARITY AQUEOUS CONCENTRATES OF 4-HEXYLRESORCINOL

(71) Applicant: JOHNSON & JOHNSON CONSUMER INC., Skillman, NJ (US)

(72) Inventors: Kalonda Tymika Johnson, Mobile, AL (US); John Lemmo, Princeton, NJ (US); Michael Southall, Pennington, NJ (US); Ping Wen, Belle Mead, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/779,854

(22) Filed: Feb. 28, 2013

(65) Prior Publication Data

US 2013/0171219 A1  Jul. 4, 2013

Related U.S. Application Data

(62) Division of application No. 13/298,816, filed on Nov. 17, 2011, now abandoned, which is a division of application No. 12/572,377, filed on Oct. 2, 2009, now Pat. No. 8,084,504.

(51) Int. Cl.
| A61K 31/05 | (2006.01) |
| A61K 8/34 | (2006.01) |
| A61Q 19/00 | (2006.01) |
| A61Q 19/08 | (2006.01) |
| A61Q 15/00 | (2006.01) |
| A61Q 17/04 | (2006.01) |
| A61Q 19/02 | (2006.01) |

(52) U.S. Cl.
CPC ............. *A61K 8/347* (2013.01); *A61K 31/05* (2013.01); *A61Q 15/00* (2013.01); *A61Q 17/04* (2013.01); *A61Q 19/00* (2013.01); *A61Q 19/02* (2013.01); *A61Q 19/08* (2013.01)

(58) Field of Classification Search
CPC ..................................................... A61K 31/05
USPC ......................................................... 514/734
See application file for complete search history.

(56) References Cited

U.S. PATENT DOCUMENTS

| 1,649,670 | A | 11/1927 | Dohme et al. |
| 2,697,118 | A | 12/1954 | Lundsted et al. |
| 3,193,507 | A | 7/1965 | Jacobs |
| 4,093,667 | A | 6/1978 | Starks |
| 4,337,370 | A | 6/1982 | Takisawa et al. |
| 4,959,393 | A | 9/1990 | Torihara et al. |
| 5,227,459 | A | 7/1993 | Pawelek et al. |
| 5,384,116 | A | 1/1995 | Pawelek et al. |
| 5,618,519 | A | 4/1997 | Pawelek et al. |
| 5,705,145 | A | 1/1998 | Miklean et al. |
| 6,797,697 | B2 | 9/2004 | Seiberg et al. |
| 6,852,310 | B2 | 2/2005 | Harichian et al. |
| 6,863,897 | B2 | 3/2005 | Love et al. |
| 6,869,598 | B2 | 3/2005 | Love et al. |
| 6,926,886 | B2 | 8/2005 | Lin et al. |
| 7,025,951 | B2 | 4/2006 | Seiberg et al. |
| 7,214,655 | B2 | 5/2007 | Seiberg et al. |
| 7,468,464 | B2 | 12/2008 | Harichian et al. |
| 8,084,504 | B2 | 12/2011 | Johnson et al. |
| 8,425,941 | B2 | 4/2013 | Yagi et al. |
| 2003/0003170 | A1 | 1/2003 | Callaghan et al. |
| 2004/0109832 | A1 | 6/2004 | Harichian et al. |
| 2004/0156873 | A1 | 8/2004 | Gupta |
| 2005/0048008 | A1 | 3/2005 | Gupta |
| 2006/0019002 | A1 | 1/2006 | Xue |
| 2006/0088608 | A1 | 4/2006 | Seiberg et al. |
| 2006/0120975 | A1 | 6/2006 | Scheri et al. |
| 2006/0210497 | A1 | 9/2006 | Harichian et al. |
| 2006/0239945 | A1 | 10/2006 | Bapat et al. |
| 2006/0264497 | A1 | 11/2006 | Zeligs |
| 2006/0269504 | A1 | 11/2006 | James |
| 2006/0292184 | A1 | 12/2006 | Richardson et al. |
| 2007/0003536 | A1 | 1/2007 | Zimmerman et al. |
| 2007/0042010 | A1 | 2/2007 | Southall et al. |
| 2007/0184017 | A1 | 8/2007 | Faryniarz et al. |
| 2007/0196523 | A1 | 8/2007 | Koganov |
| 2008/0026974 | A1 | 1/2008 | Barnhart et al. |
| 2008/0095719 | A1 | 4/2008 | Herrmann |
| 2008/0131382 | A1 | 6/2008 | Harichian et al. |
| 2008/0249029 | A1 | 10/2008 | Shapiro et al. |
| 2008/0260671 | A1 | 10/2008 | De La Torre et al. |
| 2008/0286217 | A1 | 11/2008 | Chaudhuri |
| 2008/0305059 | A1 | 12/2008 | Chaudhuri |
| 2008/0317887 | A1 | 12/2008 | Mitchell et al. |
| 2009/0087395 | A1 | 4/2009 | Lin et al. |
| 2010/0124539 | A1 | 5/2010 | Hanson |
| 2010/0189669 | A1 | 7/2010 | Hakozaki |
| 2010/0291014 | A1 | 11/2010 | Tellefsen et al. |

(Continued)

FOREIGN PATENT DOCUMENTS

| CN | 102573820 A | 7/2012 |
| DE | 101 18 894 A1 | 10/2002 |

(Continued)

OTHER PUBLICATIONS

Kolbe et al.; "4-n-butylresorcinol, a highly effective tyrosinase inhibitor for the topical treatment of hyperpigmentation"; 2013; Journal of the European Academy of Dermatology and Venereology; 27 (Suppl.1): 19-23.*

Kaur et al.; 4-Hexyl-1,3-phenylenediol, a nuclear factor-κB inhibitor, improves photodamaged skin and clinical signs of ageing in a double-blinded, randomized controlled trial; 2015; British Journal of Dermatology; 173: 218-226.*

(Continued)

*Primary Examiner* — Timothy Thomas

(57) ABSTRACT

The present invention relates to hexylresorcinol/water concentrates that are high in clarity, easily handled, and readily blended with other ingredients to form skin care compositions.

5 Claims, No Drawings

(56) References Cited

U.S. PATENT DOCUMENTS

| | | | |
|---|---|---|---|
| 2011/0081305 A1 | 4/2011 | Cochran et al. |
| 2011/0081430 A1 | 4/2011 | Kaur et al. |
| 2011/0081431 A1 | 4/2011 | Kaur et al. |
| 2011/0081433 A1 | 4/2011 | Kaur et al. |
| 2011/0171288 A1 | 7/2011 | Mohammadi et al. |
| 2012/0064149 A1 | 3/2012 | Johnson et al. |
| 2012/0128605 A1 | 5/2012 | Cochran et al. |
| 2012/0128613 A1 | 5/2012 | Cochran et al. |
| 2012/0177587 A1 | 7/2012 | Daubresse et al. |
| 2013/0071453 A1 | 3/2013 | Sojka |
| 2013/0162992 A1 | 6/2013 | Schmidt et al. |
| 2013/0165512 A1 | 6/2013 | Oddos |
| 2013/0202546 A1 | 8/2013 | Howell |
| 2014/0086859 A1 | 3/2014 | Dufort et al. |
| 2015/0272837 A1 | 10/2015 | Brillouet et al. |

FOREIGN PATENT DOCUMENTS

| | | | |
|---|---|---|---|
| DE | 10157490 A1 | 6/2003 |
| EP | 1 250 908 A2 | 10/2002 |
| EP | 1 348 418 A1 | 10/2003 |
| EP | 1 299 069 B1 | 12/2005 |
| EP | 1 974 773 A2 | 10/2008 |
| EP | 1 987 811 A1 | 11/2008 |
| EP | 2 036 565 A1 | 3/2009 |
| EP | 2 045 297 A2 | 4/2009 |
| EP | 2 100 593 A1 | 9/2009 |
| EP | 2674146 | 12/2013 |
| FR | 2 746 008 A1 | 9/1997 |
| GB | 821726 | 10/1959 |
| GB | 2438999 A | 12/2007 |
| JP | 11100324 | 4/1999 |
| JP | 2000-327557 A | 11/2000 |
| JP | 4004182 B2 | 11/2000 |
| JP | 2001 302505 A | 10/2001 |
| JP | 2004-107210 A | 4/2004 |
| JP | 2006-327965 A | 12/2006 |
| JP | 2007254412 A | 10/2007 |
| JP | 2007332116 | 12/2007 |
| JP | 2008-184431 A | 8/2008 |
| JP | 2009084164 A | 4/2009 |
| KR | 2003089598 A | 11/2003 |
| WO | WO 9853822 A1 * | 12/1998 |
| WO | WO 02/074280 A1 | 9/2002 |
| WO | WO 03/082231 A2 | 10/2003 |
| WO | WO 03080009 A1 | 10/2003 |
| WO | WO 2004/052330 A1 | 6/2004 |
| WO | WO 2004/062637 A1 | 7/2004 |
| WO | WO 2004105736 A1 | 12/2004 |
| WO | WO 2006/097223 A1 | 9/2006 |
| WO | WO 2006/128032 A2 | 11/2006 |
| WO | WO 2007/021240 A1 | 2/2007 |
| WO | WO 2008/143761 A1 | 11/2008 |
| WO | WO 2008/148016 A1 | 12/2008 |
| WO | WO 2008/153629 | 12/2008 |
| WO | WO 2009/067095 A1 | 5/2009 |
| WO | WO 2009145300 A1 | 12/2009 |

OTHER PUBLICATIONS

Database GNPD [Online] Mintel; Feb. 2009, Advanced Luminescence Serum), Database accession No. 1060752.
Database GNPD [Online] Mintel; May 2008, "Anti-oxidant Bio Moisturizing Cream SPF 15", XP002695056, Database accession No. 914469.
Database GNPD [Online] Mintel; Jan. 2004, "Max Strength Sore Throat Relief Lozenges", XP002695248, Database accession No. 252009.
Database WPI Week 200849, Thomson Scientific, London, GB; AN2008-H65100, XP002695249, & JP 2007 254412 A (Kuraray Co Ltd.) Oct. 4, 2007, Abstract.
Database WPI Week 199637 Thomson Scientific, London, GB; AN1996-368117, XP002625251, & JP H08 176004 A (Lion Corp) Jul. 9, 1996, Abstract.
Database GNPD [Online] Mintel: Oct. 2008, "Eye Recovery", XP002695054, Database accession No. 992121.
Database GNPD [Online] Mintel: Mar. 2009, "Facial Serum", XP002695055, Database accession No. 1076327.
Suzuki Y. J. et al., "Inhibition of NF-kappaB Activation by Vitamin E Derivatives", Biochemical and Biophysical Research Communications, vol. 193, No. 1, May 28, 1993, pp. 277-283, XP024767607, Academic Press Inc. Orlando, FL, US, ISSN: 0006-291X, DOI: 10.1006/BBRC.1993.1620.
Staal F. J. et al., "Antioxidants Inhibit Stimulation of HIV Transcription", Aids Research and Human Retroviruses, vol. 9, No. 4, Jan. 1, 1993, pp. 299-306, XP002037900, Mary Ann Liebert, US ISSN: 0889-2229.
EP Search Report for Application No. 10 25 1715 dated Apr. 11, 2013.
EP Search Report for Application No. 10 25 1717 dated Apr. 9, 2013.
U.S. Appl. No. 13/775,959, filed Feb. 25, 2013.
U.S. Appl. No. 13/779,814, filed Feb. 28, 2013.
Bobin, M., et al. "Effects of Color Adjuvants on the Tanning Effect of Dihydroxyacetone", J. Soc. Cosmetology Chemistry, vol. 35, pp. 265-272 (1984).
Cenizo, et al., "LOXL as a Target to Increase the Elastin Content in Adult Skin: A Dill Extract Induces the LOXL Gene Expression," Experimental Dermatology; 2006, vol. 15(8), 574-581.
Database WPI, Week 200223, Thomson Scientific, London, GB; AN 2002-174418 XP002635474, JP 2001 30205A (Kurarray Co Ltd) Oct. 31, 2001, Abstract.
Database WPI, Week 200849, Thomson Scientific, London, GB; AN 2008-H65100 XP002635473, JP 2007 254412 A (Kurarray Co Ltd) Oct. 4, 2007, Abstract.
Database WPI, Week 200930, Thomson Scientific, London, GB; AN 2009-H70662 XP 002635472, JP 2009 084164 A (Septem Soken KK) Apr. 23, 2009, Abstract.
Fukuda et al., Inhibition by Parthenolide of Phorbol Ester-induced Transcriptional Activation of Inducible Nitric Oxide Synthase Gene in a Human Monocyte Cell Line THP-1, Biochemical Pharmacology, (Aug. 15, 2000), vol. 60, No. 4, pp. 595-600.
Hall et al.; "The Solubilization of Hexylresorcinol by an Anionic-Nonionic Surfactant Mixture"; 1966; Ameri. Jour. Pharm.; 138(6): 245-8.
Hamamoto, et al., "Inhibitory effect of azelastine, a potent antiallergic agent, on release of tumor necrosis factor-a from activated human peripheral blood mononuclear cells and U937 cells," Exp Dermatol, 1993: 2: p. 231-235.
Herrmann, et al., "Blackberry Leaf Extract A New Anti-Aging Active," SOFW Journal; 2006, vol. 132(4), 42-46.
Lamaison, et al., "Tannin Content and Elastase Inhibiting Activity in the Rosaceae Family," Ann. Pharmaceutiques Francaises; 1990, vol. 48, 335-340.
Lin et al., "Theaflavin-3,3'-digallate from black tea blocks the nitric oxide synthase by down-regulating the activation of NF-κB in macrophages," European Journal of Pharmacology, vol. 367, No. 2-3, Feb. 1999, p. 379-388, XP009090023.
Liu, R. et al., "Retinoic Acid Increases Elastin in Neonatal Rat Lung Fibroblast Cultures," Am. Physiol, Society, 1993, 265(5pt. 1):L430-437.
Liu, X. et al., "Elastic Fiber Homeostasis Requires Lysyl Oxidase-like 1 Protein," Nature Genetics ; 2004, vol. 36(2), 178-182.
Ochsner et al.; "Prediction of Solubility in Nonideal Multicomponent Systems Using the UNIFAC Group Contribution Model"; 1985; Journal of Pharmaceutical Sciences; 74(6): 634-637.
Xia et al.; "Dehydration of ethyl acetate-water mixtures using PVA/ceramic composite pervaporation membrane"; 2011; Separation and Purification Technology; 77: 53-59.
Int'l Search Report for Application No. PCT/US2010/051080, dated Dec. 6, 2010.
EP Search Report for Application No. EP 10251712.5 dated May 6, 2011.
Database GNPD [Online] Mintel; Jun. 2009, "Instant Facial Sculpting", Database accession No. 1123303.
Belikov, V.G., "Pharmaceutical Chemistry", M. Higher School, 1993, vol. 1, pp. 43-47.

(56) References Cited

OTHER PUBLICATIONS

Prakash et al., "Multifunctional Ingredients: the novel face of natural" Antiaging: physiology to formulation (2006), pp. 181-188.
Colipa Guideline: Guideline for the Colorimetric Determination of Skin Colour Typing and Prediction of the Minimal Erythema! Dose (Med) Without UV Exposure, published in 2007.

*International Cosmetic Ingredient Dictionary and Handbook*, eds. Pepe, Wenninger and McEwen, (The Cosmetic, Toiletry, and Fragrance Assoc., Washington, D.C., 9th Edition, 2002), pp. 2930-36; pp. 2962-71; pp. 2979-84.
EP Search Report for Application No. EP 15161428 (JCO5130) dated Oct. 6, 2015.

* cited by examiner

HIGH-CLARITY AQUEOUS CONCENTRATES OF 4-HEXYLRESORCINOL

CROSS-REFERENCE TO RELATED APPLICATIONS

This application is a divisional of U.S. application Ser. No. 13/298,816, filed Nov. 17, 2011, which is a divisional of U.S. application Ser. No. 12/572,377, filed Oct. 2, 2009, now U.S. Pat. No. 8,084,504, the disclosure of which is hereby incorporated by reference in its entirety.

FIELD OF THE INVENTION

The present invention relates to aqueous concentrates of 4-hexylresorcinol that are high in clarity, easily handled, and readily blended with other ingredients to make personal care, consumer and household compositions.

BACKGROUND OF THE INVENTION

4-Hexylresorcinol is a compound that has been described for topical use to lighten skin, for use in oral antiseptic lozenges, and other uses. However, 4-hexylresorcinol has been described and recognized as "water insoluble." As such, formulation of 4-hexylresorcinol in combination with water has been rather limited. Typically, formulation of 4-hexylresorcinol with water has involved, for example, premixing 4-hexylresorcinol in a glycol such as ethoxydiglycol, and diluting this mixture to low concentrations of 4-hexylresorcinol by adding various other ingredients, including water. The process may also involve heating as well.

It has now been discovered, however, that mixtures of 4-hexylresorcinol and water may be made, particularly mixtures having high concentrations of 4-hexylresorcinol. Such mixtures may, for example, be used to deliver 4-hexylresorcinol to formulations without the need for additional solvents, solubilizers, and the like. In particular, an aqueous concentrate comprising about 64% to about 80% by weight of 4-hexylresorcinol is easily handled and used to make a variety formulations and compositions. Advantageously, such an aqueous concentrate is surprisingly high in clarity.

SUMMARY OF THE INVENTION

In one aspect, the invention provides a 4-hexylresorcinol aqueous concentrate comprising from about 64% to about 80% by weight of 4-hexylresorcinol, and water, wherein the aqueous concentrate is high in clarity.

The invention also provides a 4-hexylresorcinol aqueous concentrate comprising 4-hexylresorcinol and water, wherein the 4-hexylresorcinol and water are present in a concentration by weight ratio of about 1.7 to about 4, and wherein the concentrate is high in clarity.

The invention further provides a method of making a composition, comprising mixing a high clarity aqueous concentrate of 4-hexylresorcinol with a secondary composition, wherein the aqueous concentrate comprises (i) about 64% to about 80% by weight of 4-hexylresorcinol and (ii) water; and the secondary composition comprises an ingredient selected from the group consisting of hydrophobic agents, surface-tension depressing agents, fragrances, and combinations thereof.

The invention also provides a method of making a composition, comprising mixing a high clarity aqueous concentrate of 4-hexyresorcinol with a secondary composition, wherein the aqueous concentrate comprises 4-hexylresorcinol and water and the 4-hexylresorcinol and water are present in a concentration by weight ratio of about 1.7 to about 4; and the secondary composition comprises an ingredient selected from the group consisting of hydrophobic agents, surface-tension depressing agents, fragrances, and combinations thereof.

The invention further provides a composition comprising: a high clarity aqueous concentrate of 4-hexylresorcinol comprising (i) about 64% to about 80% by weight of 4-hexylresorcinol and (ii) water; and a secondary composition comprising an ingredient selected from the group consisting of hydrophobic agents, surface-tension depressing agents, fragrances, and combinations thereof.

Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Unless otherwise indicated, percentages used to express concentrations of ingredients are percentage by weight (i.e., % (W/W). Similarly concentration ratios used to express relative proportions of ingredients are also determined using percentage by weight (i.e., concentration ratios are calculated by dividing the percentage by weight of one ingredients by another). Unless stated otherwise, all ranges are inclusive of the endpoints, e.g., "from 4 to 9" includes the endpoints 4 and 9.

As used herein, "substantially free" means present in a concentration that is less than about 1%, preferably less than about 0.5%, more preferably less than about 0.1%, most preferably completely absent.

As used herein, a "product" is optionally in finished packaged form. In one embodiment, the package is a container such as a plastic, metal or glass tube or jar containing the composition. The product may further contain additional packaging such as a plastic or cardboard box for storing such container. In one embodiment, the product comprises a composition of the invention and contains instructions directing the user to apply the composition to the skin or hair.

As used herein, "topically applying" means directly laying on or spreading on outer skin, the scalp, or hair, e.g., by use of the hands or an applicator such as a wipe, roller, or spray.

As used herein, "cosmetically acceptable" means that the ingredients the term describes are suitable for use in contact with tissues (e.g., the skin or hair) without undue toxicity, incompatibility, instability, irritation, allergic response, or the like.

In certain embodiments, the aqueous concentrates and compositions of the present invention are suitable for treating signs of skin aging. As used herein, "signs of skin aging" includes the presence of lines and wrinkles, loss of elasticity, uneven skin, and blotchiness. In a particularly preferred embodiment, the sign of aging is the presence of lines and wrinkles and/or loss of elasticity.

As used herein, "treating signs of skin aging" refers to mitigating, reducing, preventing, improving, or eliminating the presence or signs of skin aging described above.

As used herein, "wrinkle" includes fine lines, fine wrinkles, or coarse wrinkles. Examples of wrinkles include, but are not limited to, fine lines around the eyes (e.g., "crow's feet"), forehead and cheek wrinkles, frown-lines, and laugh-lines around the mouth.

As used herein, "loss of elasticity" includes loss of elasticity or structural integrity of the skin or tissue, including but not limited to sagging, lax and loose tissue. The loss of elasticity or tissue structure integrity may be a result of a number of factors, including but not limited to disease, aging, hormonal changes, mechanical trauma, environmental damage, or the result of an application of products, such as a cosmetics or pharmaceuticals, to the tissue.

As used herein, "uneven skin" means a condition of the skin associated with diffuse or mottled pigmentation, which may be classified as hyperpigmentation, such as post-inflammatory hyperpigmentation.

As used herein, "blotchiness" means a condition of the skin associated with redness or erythema.

As used herein, "cosmetic" refers to a beautifying substance or preparation which preserves, restores, bestows, simulates, or enhances the appearance of bodily beauty or appears to enhance the beauty or youthfulness, specifically as it relates to the appearance of tissue or skin.

As used herein, "cosmetically effective amount" means an amount of a physiologically active compound or composition sufficient for treating one or more signs of skin aging, but low enough to avoid serious side effects. The cosmetically effective amount of the compound or composition will vary with the particular condition being treated, the age and physical condition of the end user, the severity of the condition being treated/prevented, the duration of the treatment, the nature of other treatments, the specific compound or product/composition employed, the particular cosmetically-acceptable carrier utilized, and like factors.

High Clarity Concentrates of 4-Hexylresorcinol and Water

4-Hexylresorcinol ("4-HR") is a dihydroxy phenol compound having the following structure:

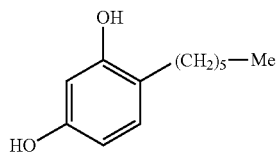

4-HR may be made by a process known in the art. An example of a suitable process is described in US Patent Application Publication No. 2006/0129002, which is herein incorporated by reference in its entirety. 4-HR is commercially available, e.g., as "SYNOVEA HR" from Sytheon of Lincoln Park, N.J.

4-HR is characterized as water-insoluble in the prior art. The inventors have, however, found that while 4-HR is clearly water-insoluble across the majority of possible concentrations/mixture ratios with water, quite surprisingly, a particular "window of compatibility" exists in which 4-HR and water form a high clarity mixture.

Accordingly, in one embodiment of the invention, a high clarity 4-hexylresorcinol aqueous concentrate comprises about 64% to about 80% by weight of 4-HR.

The remainder of the aqueous concentrate preferably comprises water. The percentage by weight of water in the concentrate may be from about 1% to about 36%, preferably from about 16% to about 36%, most preferably from about 20% to about 36%.

In another aspect of the invention, a high clarity 4-hexylresorcinol aqueous concentrate comprises 4-hexylresorcinol and water, wherein 4-hexylresorcinol and water are present in a concentration by weight ratio of about 1.7 to about 4.

In certain embodiments, the aqueous concentrate comprises about 64% to about 80% by weight 4-HR and the remainder consists essentially of water, i.e., the remainder consists of water and one or more additional ingredients that do not interfere with or diminish the high clarity character of the concentrate.

In one embodiment, such additional ingredients are limited to: (1) small concentrations of ionic salts (e.g., salts of Na, K, Cl, Ca, Mg, Zn, and the like) that are collectively present in concentrations of less than about 0.1% by weight of the concentrate, and/or (2) phenol-containing compounds such as 4-hexylbenzene-1,3-diol and others typically present as impurities in 4-HR, that are collectively present in concentrations of less than about 3% by weight of the concentrate, preferably less than 2% by weight of the concentrate, preferably less than about 1% by weight of the concentrate, most preferably less than about 0.5% by weight of the concentrate.

In certain other embodiments the additional ingredients include one or more biologically active ingredients that may, for example, be soluble in the 4-HR. Examples of suitable biologically active ingredients include salicylic acid, organic sunscreens, and retinoids.

The additional ingredients are preferably collectively present in concentrations of less than about 20% by weight, preferably less than about 10%, more preferably less than about 5%, even more preferably less than about 3%, most preferably less than about 1% by weight, of the aqueous concentrate.

In certain embodiments, the additional ingredients are collectively present in the concentrate in a concentration by weight ratio of 4-HR to additional ingredients of at least about 3.2:1, preferably at least about 6:1, more preferably at least about 12:1, more preferably at least about 20:1, and most preferably at least about 30:1.

The aqueous concentrate is high in clarity. In one embodiment, the aqueous concentrate transmits at least 25% (preferably at least 50%, more preferably at least 70%) of light having a wavelength of 700 nm through a 1 cm path length. To a typical human observer at a distance of 12 inches away, the aqueous concentrate appears clear and generally without any visible layers when placed in, for example, a conventional clear plastic 100 mL container.

Clarity may be tested using a UV-VIS spectrophotometer set at 700 nm. After a sample is allowed to equilibrate at room temperature for at least about 24 hours, it is placed in a test cell (1 cm. cuvette) and % transmission is measured using the UV-VIS spectrophotometer.

Since the aqueous concentrate is high in clarity, it does not require the addition of ingredients to increase clarity. For example, in certain embodiments the aqueous concentrate is substantially free of compatabilizers, i.e., ingredients that compatabilize hydrophobic and hydrophilic ingredients. In particular, in certain embodiments the aqueous concentrate is substantially free of one, more than one, or all of the following compatabilizers: surface tension depressing agents (surfactants and emulsifiers), $C_2$-$C_6$ alcohols (e.g., aliphatic alcohols such as ethanol and isopropanol), glycols (i.e., compounds having more than one hydroxyl group, each attached to a different carbon atom; e.g, glycerin, diols including propylene or butylene glycol); glycol ethers (e.g., diethylene glycol monoethyl ether); and hydrotropes such as sodium xylene sulfonate or sodium cumene sulfonate.

The aqueous concentrate may be prepared by mixing water, 4-HR, and any optional additional ingredients that do not diminish the high clarity the aqueous concentrate at room temperature using a magnetic stir bar, propeller mixer, etc. The order of addition is not critical. In certain embodiments, the additional ingredients are added after the 4-HR and water have been mixed together.

Methods of Use

The high clarity 4-HR aqueous concentrates can be used to make compositions, such as for products for health care, personal care, cosmetic, pharmaceutical, or household end uses.

According to another aspect of the invention, a method of making a composition is provided, which method comprises mixing a high clarity aqueous concentrate of 4-hexylresorcinol with a secondary composition, wherein the aqueous concentrate comprises (i) about 64% to about 80% by weight of 4-hexylresorcinol and (ii) water; and the secondary composition comprises an ingredient selected from the group consisting of hydrophobic agents, surface-tension depressing agents, fragrances, and combinations thereof.

Alternatively, a high clarity aqueous concentrate of 4-hexyresorcinol may be mixed with a secondary composition, wherein the aqueous concentrate comprises 4-hexylresorcinol and water present in a concentration by weight ratio of about 1.7 to about 4; and the secondary composition comprises an ingredient selected from the group consisting of hydrophobic agents, surface-tension depressing agents, fragrances, and combinations thereof.

The secondary composition comprises one or more ingredients that, when combined with the aqueous concentrate, enhances its properties for one or more end uses, e.g., renders it more cosmetically acceptable, more pharmaceutically acceptable, more suitable for bio-delivery, more surface active, more aesthetic, more convenient, etc.

The secondary composition may include one or more of the following ingredients, particularly those suitable for cosmetic, pharmaceutical, or household products: hydrophobic agents, glycols, surface-tension depressing agents, $C_2$-$C_6$ alcohols, fragrances, and combinations thereof. In certain preferred embodiments, the secondary composition includes one or more hydrophobic agents, surface-tension depressing agents, and/or fragrances.

Suitable hydrophobic agents include those hydrocarbons suitable for use in cosmetic products, such as those having branched or linear, saturated or unsaturated, carbon chains from about $C_7$ to about $C_{50}$, more preferably from about $C_8$ to about $C_{22}$, such as oils, fatty esters, fatty alcohols, waxes, or silicone oils such as ones suitable to provide emolliency, spreadability, or phase stability. In one embodiment, the hydrophobic agent does not qualify as a surface-tension depressing agent as described below.

Suitable glycols include those capable of providing humectancy, such as those exemplified above with respect to glycols suitable as compatabilizers. Suitable $C_2$-$C_6$ alcohols include those suitable to provide solvency or spreadability, also including those exemplified above as compatabilizers. Suitable fragrances include pleasant smelling mixtures of volatile aldehydes, esters and the like, including those commonly used in health care, personal care, cosmetic, pharmaceutical, or household products.

Suitable surface-tension depressing agents include any of a variety of surface-active agents capable of reducing surface tension, providing emulsification, increasing or decreasing foam, enhancing cleansing or detergency, and the like. In one embodiment, the surface-tension depressing agent is capable of reducing the surface tension of deionized water to less than about 45 dynes/cm when mixed with pure deionized water in a concentration of surface-tension depressing agent that is less than 0.5%.

The secondary composition may have additional ingredients commonly used in health care, personal care, cosmetic, pharmaceutical, or household products, e.g., dyes, chelating agents, dispersants, cosmetically or pharmaceutically active agents and the like. Non-limiting examples of cosmetically or pharmaceutically active agents for use in the secondary composition include anti-acne agents, anti-microbial agents, anti-inflammatory agents, anti-mycotic agents, anti-parasite agents, external analgesics, sunscreens, photoprotectors, antioxidants, keratolytic agents, vitamins, anti-perspiration agents, deodorants, skin (de)pigmentation agents anti-aging/anti-wrinkle agents, and pH adjusters, preservatives, and antioxidants. These active agents may be present in cosmetically effective amounts or otherwise in amounts suitable to provide suitable biological effects.

A high clarity aqueous concentrate of 4-HR may be mixed with a sufficient amount of a secondary composition to produce a formulated composition suitable for use in the health care, personal care, cosmetic, pharmaceutical, or household fields.

In one embodiment, the aqueous concentrate (alone or optionally after mixing with a secondary composition) is applied to a substrate, such as a substrate useful for wiping skin or hair. The substrate may comprise a non-woven fabric, such as those known in the art of personal care wipes.

The composition comprising the aqueous concentrate may be a single or multi-phasic system, e.g., solution, dispersion, emulsion (O/W, W/O, etc.), microemulsion, liposomal system, or gel, including any of lotions, creams, gels, sticks, sprays, ointments.

The composition may be prepared using methodologies known in the art.

Furthermore, in one embodiment, the composition may be used topically, that is, applied to mammalian skin in need of treatment for one or more signs of skin aging, acne, or other skin conditions.

The composition may be applied to skin in need of treatment according to a suitable treatment regimen, e.g., every month, every week, every other day, every day, twice a day, or the like.

It is believed that one skilled in the art can, based upon the description herein, utilize the present invention to its fullest extent. The following specific embodiments are to be construed as merely illustrative, and not limitative of the remainder of the disclosure in any way whatsoever. The following non-limiting examples further illustrate the invention.

Example I

4-HR ("SYNOVEA HR" from Sytheon of Lincoln Park, N.J.) was mixed with water in varying concentrations. Samples were allowed to sit at ambient conditions for about 7 days prior to performing visible inspection and a light transmission test as follows.

First, the visual appearance of each sample was noted. Samples were then agitated by lightly shaking to provide a representative % Transmission for each mixture. About 30 seconds after completing the agitation, each sample was placed in a 1 cm cuvette of a UV-Visible Spectrophotometer (Agilent 8453, available from Agilent technologies, Santa Clara, Calif.) set for % Transmission at 700 nm wavelength.

Results of the visual analysis and light transmission test are shown below in Table 1.

TABLE 1

| Example | % 4-HR (Source) | % Water | Concentration Ratio 4-HR:Water | APPREARANCE | TRANSMISSION % |
|---|---|---|---|---|---|
| Comparative Example, C1 | 0.65 (SYNOVEA HR) | 99.35 | 0.0065 | Cloudy mixture | |
| Comparative Example, C2 | 20 (SYNOVEA HR) | 80 | 0.25 | Large, cloudy top layer; Small, clear amber bottom layer | 0.1 |
| Comparative Example, C3 | 50 (SYNOVEA HR) | 50 | 1 | Very small clear amber topmost layer; Small, cloudy middle layer; Large, clear amber bottom layer | — |
| Inventive Example, E1 | 64 (SYNOVEA HR) | 36 | 1.78 | Homogenous, clear, amber | — |
| Inventive Example, E2 | 80 (SYNOVEA HR) | 20 | 4 | Homogenous, clear, amber | 75 |
| Comparative Example, C4 | 50 (Sigma-Aldrich) | 50 | 1 | Very small clear amber topmost layer; Small, cloudy middle layer; Large, clear amber bottom layer | — |
| Inventive Example, E3 | 64 (Sigma-Aldrich) | 36 | 1.78 | Homogenous, clear, amber | — |

The results show that, while the prior art characterizes 4-HR as water insoluble, surprising compatibility exists for the 4-HR/water mixtures containing 64%-80% 4-HR (4-HR to water weight ratios of 1.78 to 4).

Example II

4-Octylresorcinol and 3-methoxyphenol (from Sigma-Aldrich of St. Louis, Mo.) were separately mixed with water at 50% and 75% concentrations. None of the mixtures were clear, and all showed "layering" similar to what was observed for Comparative Example, C3 (above).

Example III

The following composition according to the invention was made using the ingredients shown in Table 2.

TABLE 2

| TRADE NAME | INCI NAME | Formula % |
|---|---|---|
| Purified Water | Water | 75.66 |
| Pemulen TR-1 | Acrylates/C10-30 Alkyl Acrylate Crosspolymer | 0.08 |
| Edeta BD | Disodium EDTA | 0.1 |
| Hyaluronic Acid BT | Sodium Hyaluronate | 0.1 |
| Dry Flo Pure | Aluminum Starch Octenylsuccinate | 1 |
| Butylene Glycol | Butylene Glycol | 2 |
| Glycerin 99.5% | Glycerin | 5 |
| Olivem 1000 | Cetearyl Olivate; Sorbitan Olivate | 0.5 |
| Aristoflex AVC | Ammonium Acryloyldimethyltaurate/VP Copolymer | 0.6 |
| Sodium Hydroxide | Sodium Hydroxide | 0.04 |
| Purified Water | Water | 0.36 |
| DC 345 Fluid | Cyclopentasiloxane; Cyclohexasiloxane | 5 |
| DC 200 50cps | Dimethicone | 2 |
| DC 1403 | Dimethicone; Dimethiconol | 2 |
| Neolone MxP | Phenoxyethanol; Methylparaben; Propylparaben; Methylisothiazolinone | 0.6 |
| *Portulaca* Extract | *Portulaca Oleracea* Extract; Butylene Glycol; Water | 1 |
| Prodew 300 | Sodium Lactate; Sodium PCA; Sorbitol; Proline | 0.6 |
| Sepitonic M3 | Magnesium Aspartate; Zinc Gluconate; Water; Copper Gluconate; Phenoxyethanol | 1 |
| Alpha Bisabolol 2/012685 | Bisabolol | 0.25 |
| Seamollient | Water; *Chondrus Crispus* (Carrageenan) Extract; Propylene Glycol; Citric Acid | 1 |
| Net-DG | Dipotassium Glycyrrhizate | 0.01 |
| Fragrance | Fragrance | 0.1 |
| Inventive 4-HR (75%) water (25%) hi clarity aqueous mixture | 4-Hexylresorcinol and water | 1 |

The composition was made as follows:
1. WATER was added to the main mixing vessel and the stirrer was turned on.
2. PEMULEN TR-1 POLYMER was sprinkled into the mixing vessel, and the ingredients were mixed until completely dispersed (15-20 min).
3. A Water, EDTA and Hyaluronic acid premix was made. EDETA BD was added to water in a separate beaker and mixed until completely dissolved. The Hyaluronic acid premix was added and the ingredients were mixed until uniform (30 min).
4. Glycerine was added into the water phase and mixed until uniform.
5. The mixture was heated to 70-75° C.
6. Olivem 1000 was added; the ingredients were then mixed for 5 min. and cooling to 60-65° C. was started.
7. At 60-65° C. ARISTOFLEX AVC was added, and the ingredients were mixed until completely dispersed (20 minutes). The temperature was maintained at 60-65° C.
8. SODIUM HYDROXIDE (10% soln) was added to neutralize the water phase.

9. Cooling to below 60° C. was begun.
10. After cooling to 60° C., DOW CORNING 200 50 cst was added and the ingredients were mixed until uniform.
11. DOW CORNING 345 was added to the water phase and mixed for 10 minutes.
12. DOW CORNING 1403 Fluid was added and mixed for 15 minutes or until uniform.
13. After cooling to below 35° C., the following were added one by one: NEOLONE MxP, PORTULACA EXTRACT, PRODEW 300, Alpha Bisabalol, Water, EDTA; Hyluronic Acid Premix (step-3), Sepitonic M3, and Seamollient. The resulting mixture was mixed until uniform.
14. After ensuring there were no lumps, the Dry flo pure (item 6) premixed with Butylene Glycol (item 7) was added.
15. The Net-DG premixed with fragrance was then added and the ingredients were mixed until uniform.
16. In a separate vessel, the 75% 4-HR and water were mixed to form a high clarity aqueous concentrate, which was then added to the other ingredients.
17. The resulting composition was then homogenized for 3 min.

Example IV

The composition of Example III was evaluated for topical anti-inflammatory activity on human epidermal equivalents. Epidermal equivalents (EPI 200 HCF) that were multilayer and differentiated epidermis consisting of normal human epidermal keratinocytes (MatTek, Ashland, Mass.) were used. Upon receipt, the epidermal equivalents were incubated for 24 hours at 37° C. in maintenance medium without hydrocortisone. Equivalents were topically treated (2 mg/cm$^2$) with the composition of Example III for 2 hours before exposure to 100 ng/mL of Tumor Necrosis Factor-$\alpha$ (TNF$\alpha$, Sigma-Aldrich of St. Louis, Mo.). Equivalents were incubated for 24 hours at 37° C. with maintenance medium. The supernatants were analyzed for IL-8 cytokine release using commercially available kits (Upstate Biotechnology, Charlottesville, Va.). The results are depicted on Table 3.

TABLE 3

| Treatment | Percent Inhibition of Skin Inflammation |
|---|---|
| Placebo | 14.88 |
| Example III Composition | 77.89** |

**Indicates significant difference from placebo treated using a student's t-Test with significance set at P < 0.05.

The composition of Example III significantly reduced inflammation.

The invention claimed is:

1. A method of treating a sign of skin aging, which comprises (i) preparing a formulated composition by mixing (a) high clarity aqueous concentrate consisting of water and from about 64% to about 80% by weight of 4-hexylresorcinol and (b) a secondary composition comprising a cosmetically or pharmaceutically active agent selected from the group consisting of anti-acne agents, anti-microbial agents, anti-inflammatory agents, anti-mycotic agents, anti-parasite agents, external analgesics, sunscreens, photoprotectors, antioxidants, keratolytic agents, vitamins, anti-perspiration agents, deodorants, skin depigmentation agents, anti-aging agents, anti-wrinkle agents, pH adjusters, preservatives, and anti-oxidants; and (ii) topically applying said formulated composition to skin in need of treatment for one or more signs of skin aging.

2. The formulated composition of claim 1, wherein the cosmetically or pharmaceutically active agent is selected from the group consisting of anti-aging agents, anti-wrinkle agents and anti-oxidants.

3. The method of claim 1, wherein the formulated composition is in the form of solution, dispersion, emulsion, microemulsion, liposomal system, gel, lotion, cream, stick, spray, or ointment.

4. A method of making a composition, comprising mixing a high clarity aqueous concentrate of 4-hexylresorcinol with a secondary composition, wherein the aqueous concentrate consists of (i) about 64% to about 80% by weight of 4-hexylresorcinol and (ii) water; and the secondary composition comprises an ingredient selected from the group consisting of hydrophobic agents, surface-tension depressing agents, fragrances, and combinations thereof.

5. A method of making a composition, comprising mixing a high clarity aqueous concentrate of 4-hexylresorcinol with a secondary composition, wherein the aqueous concentrate consists of (i) about 64% to about 80% by weight of 4-hexylresorcinol and (ii) water; and the secondary composition comprises a cosmetically or pharmaceutically active agent selected from the group consisting of anti-acne agents, anti-microbial agents, anti-inflammatory agents, anti-mycotic agents, anti-parasite agents, external analgesics, sunscreens, photoprotectors, antioxidants, keratolytic agents, vitamins, anti-perspiration agents, deodorants, skin depigmentation agents, anti-aging agents, anti-wrinkle agents, pH adjusters, preservatives, and anti-oxidants.

* * * * *